United States Patent
Odogba et al.

(10) Patent No.: US 6,919,568 B2
(45) Date of Patent: Jul. 19, 2005

(54) METHOD AND APPARATUS FOR IDENTIFYING COMPOSITE DEFECTIVE PIXEL MAP

(75) Inventors: Jibril Odogba, Wales, WI (US); Ken Scott Kump, Waukesha, WI (US); Ping Xue, Cottage Grove, WI (US); Donald Fayette Langler, Brookfield, WI (US); John C. French, Wauwatosa, WI (US); John Moore Boudry, Waukesha, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 288 days.

(21) Appl. No.: 10/408,853

(22) Filed: Apr. 8, 2003

(65) Prior Publication Data

US 2004/0200969 A1 Oct. 14, 2004

(51) Int. Cl.⁷ .............................. G01T 1/24; H05G 1/64
(52) U.S. Cl. .............................. 250/370.09; 250/336.1; 250/370.01; 382/130; 382/131; 382/132; 378/98.8
(58) Field of Search .................. 250/370.09, 336.1, 250/370.01; 382/130, 131, 132; 378/98.8

(56) References Cited

U.S. PATENT DOCUMENTS

| | | |
|---|---|---|
| 4,996,413 A | 2/1991 | McDaniel et al. |
| 5,047,863 A | 9/1991 | Pape et al. |
| 5,272,536 A | 12/1993 | Sudo et al. |
| 5,657,400 A | 8/1997 | Granfors et al. |
| 5,854,655 A | 12/1998 | Watanabe et al. |
| 6,529,618 B1 * | 3/2003 | Ohara et al. ................. 382/132 |
| 6,661,456 B1 * | 12/2003 | Aufrichtig et al. .......... 348/247 |
| 6,663,281 B2 * | 12/2003 | Aufrichtig et al. .......... 378/207 |
| 2002/0149684 A1 * | 10/2002 | Leveau-Mollier ........... 348/246 |
| 2004/0096125 A1 * | 5/2004 | Alderson et al. ........... 382/312 |

OTHER PUBLICATIONS

Philips Cardiac MR Research Network, fieldstrength, pp. 14–15, Issue 9, Jul. 2000, Eltjo Haselhoff, Ph.D.

* cited by examiner

Primary Examiner—David Porta
Assistant Examiner—Christine Sung
(74) Attorney, Agent, or Firm—Quarles & Brady LLP; Carl Horton

(57) ABSTRACT

An apparatus for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, after signals are generated, the processor automatically using intensity signals corresponding to other than the bad pixel set to generate replacement intensity signals for each of the bad pixel set pixels thereby generating a corrected image, the apparatus for identifying additional bad pixels, the apparatus comprising a processor that, after the image data is collected, examines at least one of the initial image and the corrected image to identify a likely additional bad pixel set including pixels that have unexpected values and an interface for indicating the likely bad set to a system user.

20 Claims, 4 Drawing Sheets

Bad Pixel Threshold Table (100)

102 — Bad Pixel Threshold Table
104 — Imaging Type
106 — Acceptable Max Pixel Variance

| X-ray Energy | Imaging Type | Acceptable Max Pixel Variance |
|---|---|---|
| 1 | Cardiac | XX |
|  | Mamographic | YY |
|  | Angiographic | ZZ |
| ... |  |  |
| 2 | Cardiac | XX |
|  | Mamographic | YY |
|  | Angiographic | ZZ |
| ... |  |  |
| 3 |  |  |
| ... |  |  |
| XXX | ... |  |

Fig. 4

METHOD AND APPARATUS FOR IDENTIFYING COMPOSITE DEFECTIVE PIXEL MAP

STATEMENT REGARDING FEDERALLY SPONSORED RESEARCH

Not applicable.

CROSS-REFERENCE TO RELATED APPLICATIONS

Not applicable.

BACKGROUND OF THE INVENTION

The present invention relates to X-ray detectors and, more particularly, to bad pixel identification in large area solid state X-ray detectors.

Large area solid state X-ray detectors have been developed in the X-ray art. Such detectors typically comprise a scintillating layer in contact with an array of photodiodes, organized in rows and columns, each with an associated FET switch. The scintillating layer converts X-ray photons to light photons. The array of photodiodes converts light photons to electrical intensity signals. The photodiodes are initially separately charged by connecting each of the photodiodes to a stable voltage source characterized by a known potential. Each photodiode is connected to the source via a dedicated FET switch (i.e., there is a separate FET switch for each of the photodiodes).

During operation, the photodiodes are isolated by turning off their FET switches. Upon exposure to X-rays, the scintillating layer produces light that discharges each photodiode in proportion to the X-ray exposure at the position of the diode. After a short exposure period, the diodes are recharged by reconnecting the diodes to the stable voltage source. The charge used to restore each diode to its initial voltage is measured by a sensing circuit, and the measured value is digitized and stored as an imaging array of digital intensity signals. After acquisition, the resulting intensity signal array comprises an X-ray image of the distribution of X-rays impinging on the detector. Hereinafter each photodiode-FET switch pair will be referred to as a detector "pixel".

Solid state X-ray detectors of the type described above include a large number (e.g., several million) of detector pixels wherein each pixel generates a separate intensity signal. Because of non-uniformities in detector manufacturing processes, different regions of a detector are typically characterized by different readout behavior due to differences in the intrinsic characteristics and physical limitations of the detector. In order to produce diagnostic quality images, the differences in intrinsic characteristics and physical limitation must be compensated for. To this end, typical compensation algorithms often include subtracting a pixel specific offset value from each original uncorrected pixel intensity value and multiplying the result by a pixel specific gain correction factor.

The range of offset values and gain correction factors is limited and therefore, not surprisingly, at least some fraction of detector pixels generate signals that cannot be corrected to reflect actual X-ray intensity using the offset values and gain factors. These defective pixels are referred to hereinafter as "bad pixels".

Fortunately, perfect detectors are not required to generate medical X-ray images. In this regard, the minimum size of objects that can be clearly seen in a medical image is determined by an imaging system detective quantum efficiency (DQE). For large area solid state detectors the factors affecting the detector's DQE include lateral spread of light photons and of secondary X-ray photons in the scintillating layer, the finite size and noise properties of the detector pixels. Thus, scintillating layer structure and pixel size can be designed so that a detector's DQE is adequate to generate images in which the smallest object of interest is observable. More specifically, to provide an adequate DQE, pixel size can be chosen so that even the smallest objects of interest to be imaged spread signal over more than one detector pixel (i.e., detector element). Where object signal is spread over more than one pixel, unless large numbers of "bad pixels" are aggregated in sizable clusters, the loss of information due to bad pixels is minimal.

Nevertheless, because signal intensity from bad pixels is either independent of X-ray exposure or depends on X-ray exposure in a way that is different than signal intensities generated by adjacent good pixels, the effects of bad pixels are visually noticeable as artifacts (e.g., pixels, lines etc) in resulting images and hence degrade diagnostic usefulness.

The industry has developed several ways in which to identify and replace bad pixels with suitable intensity values that substantially mitigate the effects of bad pixels. The process of compensating for bad pixels is generally a two step process including identifying bad pixels and then replacing the bad pixel intensities. With respect to identifying bad pixels, typically, prior to shipping detectors to customers, detector manufacturers perform tests on each manufactured detector to identify a "manufacturer's bad pixel map". The manufacturer's map is provided to the customer along with the detector and is used by an image processor to correct for known bad pixels after image data is collected.

It is also known that detector elements have varying useful lives and that at least a percentage of detector pixels that are initially good when shipped by a manufacturer will become bad during detector use. For this reason, various tests have been devised to identify bad pixels in addition to the pixels that are included in the manufacturer's map and that can be added to the manufacturers map to provide a combined map.

One method for identifying additional bad pixels is to find each pixel that requires an offset value (defined as the signal obtained in the absence of X-ray exposure) or gain factor (defined as the signal obtained per unit of X-ray exposure) that lies outside an acceptable limit. Here, a pixel will be identified as bad if its offset value and/or gain factor lies outside a range that can be corrected with available readout electronics.

According to at least one method, an image of pixel offset values is created by averaging together several images obtained in the absence of X-ray exposure (sometimes referred to as "dark images"). Pixels whose offset values are either above the maximum correctable offset or below the minimum correctable offset value are identified as bad pixels.

An image of gain factors is created by averaging together several images obtained with uniform X-ray exposure, subtracting the offset value image, and normalizing to a value (typically the median). The gain factor image has pixel values that are proportional to corresponding pixel gains. Pixels whose gain factor are above a maximum correctable gain factor or below a minimum correctable gain factor are also identified as pixels with bad gain and also added to a bad pixel map.

These processes of identifying bad pixels from either offset, gain, or other tests can be performed at different times in the life of a detector. Performed during the detectors manufacturing is dubbed the "manufacturing bad pixel map", performed on an installed product during a calibration is dubbed the "system bad pixel map"; performed on an installed product running as a background task when a system image processor detects that the imaging system is idle (i.e., when the detector is not in use), is a "run-time bad pixel map".

A pixel may only be defective at certain X-ray energy ranges. For instance, assuming an X-ray source that can generate X-rays at five different energy levels, a detector pixel may be defective at one of the five levels and not at the other four. For this reason, at least some systems store several different energy dependent bad pixel maps and the appropriate bad pixel map is selected as a function of the X-ray energy level used during data acquisition.

During image processing, after pixel intensity data has been collected, for each bad pixel in the combined map, the image processor uses pixel intensity data corresponding to surrounding good pixels to generate a replacement pixel intensity value. Any of several different replacement intensity algorithms may be used to identify replacement pixel values such as weighted interpolation or extrapolation. One exemplary intensity determining algorithm is described in U.S. Pat. No. 5,657,400 which is entitled "Automatic Identification And Correction Of Bad Pixels In A Large Area Solid State X-ray Detector" which issued on Aug. 12, 1997 and which is commonly owned with the present invention.

While bad pixel correction processes clearly result in diagnostically more useful images, at some point the number and/or pattern of bad pixels exceeds minimum detector performance needed to ensure diagnostic quality images and the detector itself has to be repaired or replaced. Thus, for instance, when 10% of detector pixels are bad, the detector may be considered defective. As another instance, where a detectors detecting surface is dividable into one hundred separate sections including ten rows and ten columns, where 15% of the pixels in any one of the sections are bad, the detector may be considered defective.

Despite all of the detector tests described above, some bad pixels have been known to escape detection because at the time of the test, the pixel intensity values corresponding to these pixels pass the limits used to run the tests. In addition, despite meeting test requirements at the times the tests are run, some pixels operate differently during subsequent data acquisition processes. Bad pixels that are not included in the combined bad pixel map for any reason are referred to hereinafter as "maskable bad pixels".

To compensate for maskable bad pixels it is known to provide an image to a system user via an interface display where the image has been corrected for each bad pixel in a manufacturer's bad pixel map. Thereafter, visually examining the corrected image via the display, the user is provided tools to select additional image pixels that the user believes to be bad. After the user selects all of the pixels that the user believes are bad, the user selected pixels are added to the manufacturer's bad pixel map and the updated map is then useable for subsequent correction processes.

While the above system and methods clearly increase the diagnostic usefulness of resulting-images, unfortunately the system and methods have several shortcomings. First, while maskable bad pixels do show up in images prior to replacement, it is tedious for a system user to identify each maskable bad pixel in an image for replacement. For instance, assume that 300 different maskable bad pixels are evident in an image when a system user observes the image. Independently selecting each of the 300 bad pixels either through specification of detector coordinates (e.g., row and column) or via a graphical user interface such as a mouse controlled cursor is extremely burdensome and, in many cases, will be foregone by the system user.

Second, even where a system user elects to earmark maskablebad pixels, the efficacy of earmarking will depend on how accurately the user perceives adjacent signal disparities. Thus, if a user's perception is slightly off, the user may earmark certain pixels as bad that in fact, by objective standards, would not be considered bad. The danger here is that a poorly perceiving user may cause the combined bad pixel map to be erroneously modified which would thereafter be used to degrade subsequent images generated by the system.

Third, it is known that different anatomical structures have different X-ray contrasts. For instance, cardiac X-ray images may be characterized by various vessel walls and adjacent fluids may be characterized by a first level of expected contrast (e.g., where disparate contrast between adjacent pixels is expected) while mammographic images may be characterized by vessels and fluids in which a second level of contrast is expected. Here, the threshold of visibility and contrast that should be applied when identifying maskable bad pixels should be different and should depend on the anatomical structure being imaged. In a system that relies on subjective standards applied by a system user to identify bad pixels, optimal thresholds most likely will not be applied.

SUMMARY OF THE INVENTION

The invention includes an apparatus for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, after signals are generated, the processor automatically using intensity signals corresponding to other than the bad pixel set to generate replacement intensity signals for each of the bad pixel set pixels thereby generating a corrected image, the apparatus for identifying additional bad pixels, the apparatus comprising a processor that, after the image data is collected, examines at least one of the initial image and the corrected image to identify a likely additional bad pixel set including pixels that have unexpected values and an interface for indicating the likely bad set to a system user.

The invention also includes a method for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, after signals are generated, the processor automatically using intensity signals corresponding to other than the bad pixel set to generate replacement intensity signals for each of the bad pixel set pixels thereby generating a corrected image, the method for identifying additional bad pixels, the method comprising the steps of, after the image data is collected, automatically examining at least one of the initial image and the corrected image via a processor to identify a likely bad pixel set including pixels that have unexpected intensity values and indicating the likely bad set to a system user via an interface.

The invention further includes a method for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, the method comprising the steps of, after signals are generated examining initial intensity signals corresponding to other than the bad pixel set via the imaging processor to identify a likely bad pixel set including pixels that have unexpected values, using the intensity signals corresponding to other than the bad pixel set to generate replacement intensity signals for each of the bad pixel set pixels thereby generating a corrected image, providing the corrected image via an interface, identifying the likely bad set on the corrected image and monitoring the interface for selection of user identified bad pixels, when user identified bad pixels have been identified, adding the user identified bad pixels to the bad pixel set to generate an updated bad pixel map, using the intensity signals corresponding to other than the updated bad pixel map to generate replacement intensity signals for each of the updated bad pixel map pixels thereby generating a corrected image and presenting the corrected image to the system user via the interface.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE DRAWINGS

FIG. 4 is an exemplary bad pixel identification threshold table used with the present invention.

DESCRIPTION OF THE PREFERRED EMBODIMENT

Figure 1:
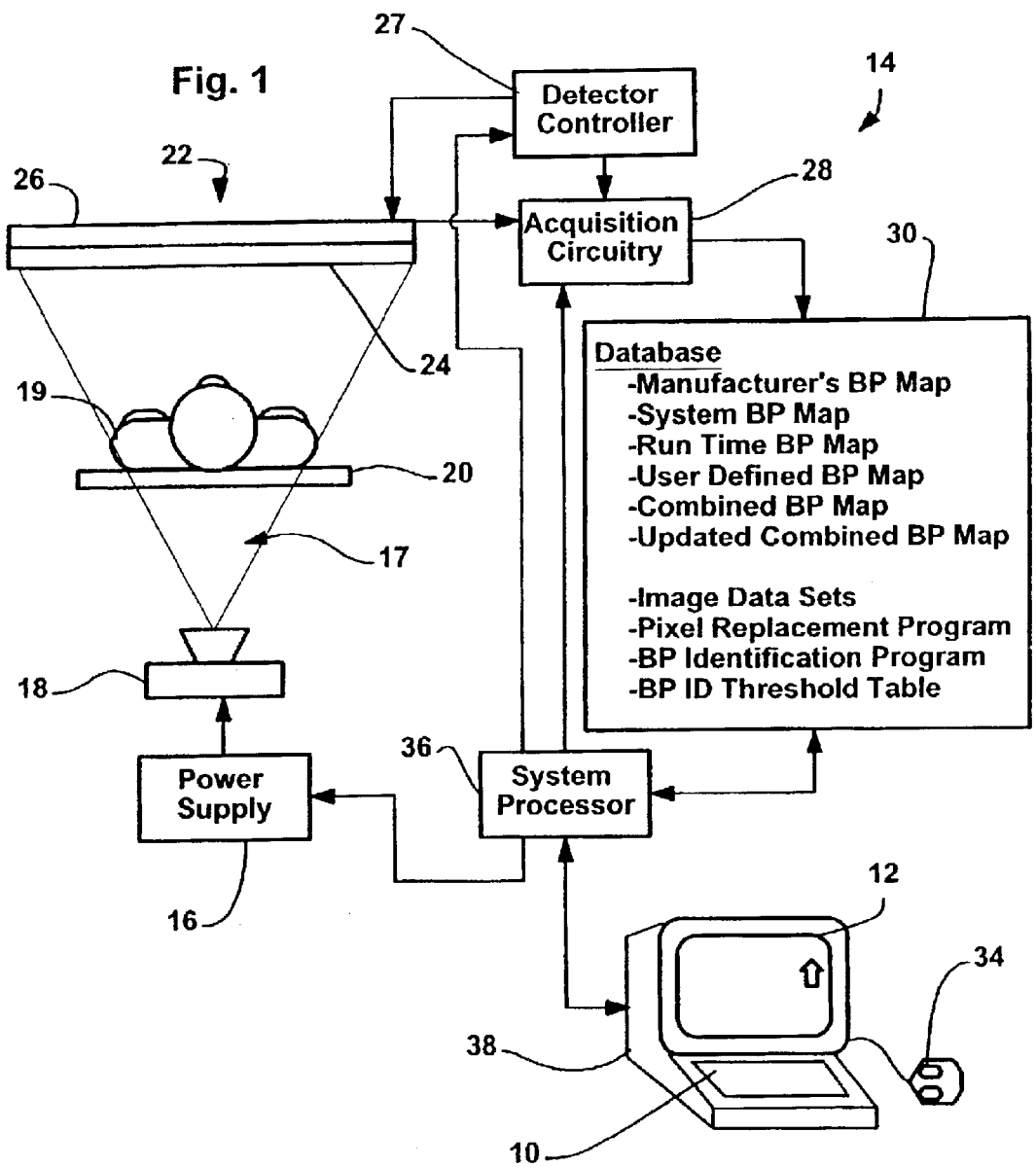
FIG. 1 is a schematic diagram illustrating an exemplary imaging system according to the present invention.

Referring now to the drawings, and more specifically, referring to FIG. 1, the present invention will be described in the context of exemplary X-ray imaging system 14 which includes an X-ray source 18, a large area solid state X-ray detector 22, a patient support table 20, a power supply 16, a detector controller 27, acquisition circuitry 28, a system processor 36, a database 30, and a user interface generally identified by numeral 38. As illustrated, when X-ray source 18 is excited by power supply 16, source 18 emits an X-ray beam 17. Source 18 and detector 22 are juxtaposed on opposite sides of an imaging area such that the X-ray beam 17 emanating from source 18 is directed toward a detecting surface of detector 22 and subtends the detecting surface.

Patient support table 20 is generally positioned within X-ray beam 17 such that, when a patient 19 is positioned for support on table 20 within the imaging area, the patient or, at least, a portion of the patient of interest, resides within X-ray beam 17. Thus, the portion of the beam that is transmitted through the patient 19 impinges upon the X-ray detector detecting surface.

In general, detector 22 includes a scintillating layer or crystal 24 and a photo detector array 26. As well known in the imaging arts, when X-ray photons impinge upon scintillating layer 24, layer 24 converts the X-ray photons into light. Photo detector array 26 includes a matrix of detector elements (not separately labeled) that are arranged on an amorphous silicon wafer. The detector elements are typically arranged to form a two-dimensional array of element rows and columns. For example, a typical high resolution X-ray detector may include two thousand rows and a similar number of columns of separate detector elements. Construction and operation of the detector elements is well known in the art and therefore, in the interest of simplifying this explanation, will not be described here in detail.

For a more detailed explanation of the design and operation of the detector elements, reference should be had to U.S. Pat. No. 4,996,413 which issued on Feb. 26, 1991 and which is entitled "Apparatus and Method for Reading Data from an Image Detector", which is incorporated herein by reference for its teachings regarding detector element design and operation. For the purposes of the present invention, it should suffice to say that each of the multiple detector elements in array 26 detects light generated by a proximate portion of scintillating layer 24 and generates an element signal having a magnitude that depends upon the intensity of light sensed. Hereinafter, consistent with the background description above, the detector elements will be referred to as detector pixels or simply pixels.

Referring still to FIG. 1, detector 22 is linked to acquisitions circuitry 28 which is in turn linked to database 30. As its label implies, acquisition circuitry 28 is configured to acquire data from detector 22 during a data acquisition process and, when data is acquired from detector 22, circuitry 28 stores the acquired data in database 30 as separate X-ray images or image data sets.

System processor 36 controls overall operation of imaging system 14. In this regard, processor 36 is linked to each of power supply 16, acquisition circuitry 28, and database 30. In addition, processor 36 is linked to detector controller 27 for controlling operation of detector 22 during data acquisition, and also, during various commissioning procedures. Moreover, processor 36 is linked to system user interface 38 for two-way communication therewith. Thus, processor 36 can receive system commands via interface 38 and also provides information to interface 38 for presentation to a system user.

Interface 38 is a computer work station including a display 12 and some type of input device or devices that allow a system user to provide control information to system 14. In FIG. 1, exemplary input devices include a keyboard 10 and a mouse 34 that can be used to control a pointing and selection cursor on display 12 in a manner known in the computing arts.

Figure 2:
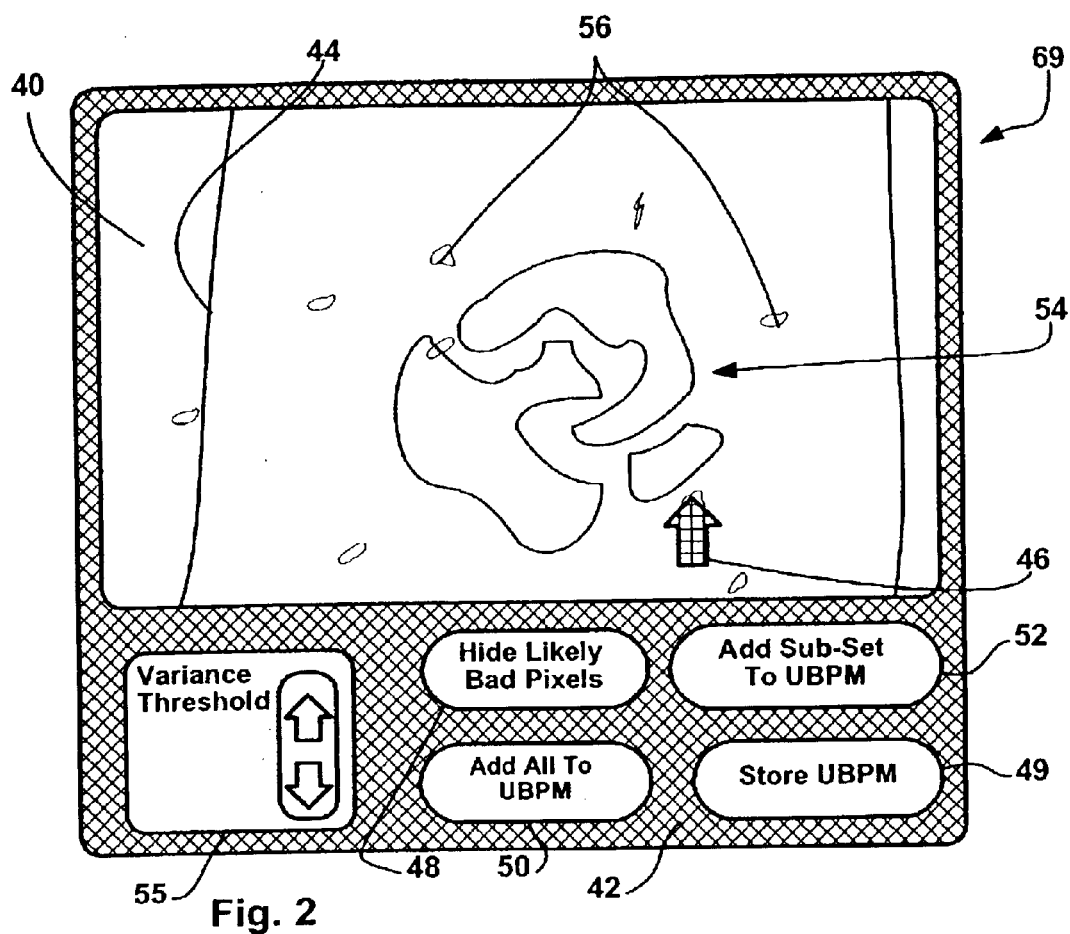
FIG. 2 is an exemplary screen shot that may be provided via the display of FIG. 1 according to the present invention.

An exemplary display screen shot 69 is illustrated in FIG. 2. In at least some embodiments of the invention, an exemplary screen shot will include two different areas including an image area 40 and a user interface area 42 at the bottom of the screen shot. As its label implies, image area 40 is used to provide X-ray images to a system user for examination. Similarly, as its label implies, interface area 42 is provided to facilitate interfacing with a system user and, to that end, a plurality of selectable icons 48, 49, 50, 52, 55, etc. are provided. Other interface screen shot layouts are contemplated as well as other types of interfaces.

Referring once again to FIG. 1, in addition to being used to store images, database 30 is also used to store various other types of information required by processor 36 to perform methods according to the present invention. In this regard, one other type of information that may be stored in database 30 includes various types of bad pixel (BP) maps required by processor 36. For instance, each of a manufacturers' BP map, a system BP map, a runtime BP map, and a combined BP map (i.e., the combined map including the combination of bad pixels in each of the manufacturers, system, and runtime maps) may be separately stored in database 30. In addition, once a user defines a BP map, the user-defined BP map may be stored in database 30. Furthermore, after a user-defined BP map has been generated, an updated combined BP map including a combination of the combined BP map and the user-defined BP map may be stored in database 30. Herein it is assumed that a plurality of each of the map types above (e.g., manufacturer's, system, run time, user defined, combined and updated combined) may be stored in database 30, a separate one of each map type corresponding to each distinct X-ray energy range (e.g. cardiac, mammography, angiography, radiograpy) used with system 14. Moreover, user defined maps may be stored for different system users so that, for instance, three separate radiologists may store their own user defined maps for detector 22.

Another type of information stored in database 30 includes programs required by processor 36 to generate replacement pixel values for pixels in a bad pixel map. There are many different algorithms that may be used to generate replacement pixel values and the present invention should not be limited to any one or sub-set of the algorithms. For better understanding of an exemplary algorithm that may provide the basis of a pixel value replacement program run by processor 36, reference should be had to U.S. Pat. No. 5,657,400 which issued on Aug. 12, 1997 and which is entitled "Automatic Identification and Correction of Bad Pixels in a Large Area Solid State X-Ray Detector" which is Incorporated herein by reference for its teaching regarding pixel replacement algorithms.

Yet one other type of information that may be stored in database 30 includes bad pixel identification threshold information that can be used for processor 36 to identify a set of likely bad pixels in an X-ray image by comparing pixel intensity values with the values of neighboring pixels.

Generally speaking, referring again to FIG. 1, assuming that, initially, a combined BP map is stored in database 30, imaging system 14 can be used to acquire X-ray image data (i.e., a set of pixel intensity signals) which is stored as an image data set in database 30. Thereafter, processor 36 runs a pixel signal replacement program to generate replacement pixels in the image set for each pixel in a combined BP map, and stores the resulting data set as a corrected image data set in database 30.

Referring also to FIG. 2, processor 36 can then be used to display a corrected image corresponding to the image data set within image area 40. The exemplary image in FIG. 2 includes an outline 44 of a patient's torso and some internal anatomical structure 54. Each of the outline 44 and anatomical structure 54 have relative bold lines to distinguish that structure from other information provided within image space 40.

As described above, where any of the detector 22 pixels (e.g. detector elements) are defective or bad and those pixels are not included in a bad pixel map, the pixel signal values corresponding to the bad pixels will not be replaced and, as a result, will show up as discontinuities or irregularities in the resulting image provided within image space 40. In FIG. 2, irregularities or discontinuities corresponding to maskable bad pixels that are not included in the combined bad pixel map have been highlighted by thin lines. Two areas having maskable bad pixels are identified by numeral 56.

It should be appreciated that, unless purposefully highlighted as in FIG. 2, the irregularities and discontinuities that are caused by maskable bad pixels will not show up as obviously as they are illustrated in FIG. 2. For instance, instead of showing up as outlined irregularities as in FIG. 2, irregularities may simply include one pixel or a set of adjacent pixels that have lower or higher intensity values than would be expected given the intensities of pixels surrounding the bad pixels. In other words, the effects of maskable bad pixels would simply be disparities in pixel shading.

Referring still to FIGS. 1 and 2, according to the present invention, processor 36 identifies a set of likely bad pixels (e.g., areas 56 in FIG. 2) as a function of differences in signal intensities generated by detector pixels, and then indicates the likely bad pixel set to the system user. For instance, in FIG. 2, processor 36 may provide the image illustrated in space 40 where likely bad pixels are earmarked by a thin line identifying one or a plurality of adjacent bad pixels. Thus, while likely bad pixels may not show up quite as obviously as illustrated in FIG. 2 without the aid of processor 36, after processor 36 performs a method according to the present invention, the likely bad pixels will indeed be earmarked as illustrated according to at least one embodiment of the invention to help a system user identify the likely maskable bad pixel set.

It is contemplated that a system user may wish to be able to observe an image with a likely set of bad pixels highlighted as in FIG. 2 or, in the alternative, to be able to observe an image without the likely set of bad pixels highlighted. For this reason, in at least some embodiments of the invention, a toggle button may be provided to allow a user to toggle between an image where likely bad pixels are not highlighted and another image like the image of FIG. 2 where likely bad pixels are highlighted. In FIG. 2, the toggle button is provided as a mouse selectable icon 48 which, when selected, eliminates the likely bad pixel set highlighting effect.

To select icon 48 or, for that matter, to select any other icons provided and displayed, mouse 34 (see FIG. 1) may be used to move cursor 46 on the display screen 12 to point to whatever a user wishes to select and then some type of mouse selection activation may be performed.

At least some embodiments of the present invention also contemplate that a system user may wish to select only a sub-set of pixels that a processor 36 identifies as a likely bad set of pixels. Here, the user may move cursor 46 to any of the highlighted likely bad pixels in image space 40 and, by clicking one of the mouse buttons, select that highlighted irregularity. Once a highlighted irregularity has been selected in at least some embodiment of the invention, processor 36 may earmark the selected irregularity in a second manner which is different than the way irregularities are initially highlighted on screen 12. For instance, the initial thin outline of each irregularity may be a first color while user selected/accepted irregularities may be outlined using a second color.

After one or more likely bad pixel irregularities have been earmarked in space 40, the user may select icon 52 thereby indicating to processor 36 that the user is selecting only the earmarked sub-set of likely bad pixels displayed within space 40. Where a user wants to accept all of the likely bad pixels highlighted on display 12 by processor 36, the user may select icon 50.

In addition to being able to select a sub-set or all of the processor identified likely bad pixel set, it is contemplated that a user may also wish to independently identify other image pixels as bad pixels by applying subjective user criteria. Here, in at least some embodiments of the invention, a user may use cursor 46 to select pixels in addition to the processor identified pixels for inclusion in the user selected bad pixel set. As in the case of processor identified and user accepted bad pixels, user identified and selected bad pixels may be highlighted in some fashion to distinguish those pixels from others that have not been selected.

Once all or a sub-set of the processor identified likely bad pixels have selected and accepted by the system user, the user selects store icon 49 at which point processor 36 stores the user defined BP map in database 30 for subsequent use. In addition, processor 36, in at least one embodiment of the present invention, combines the user-defined BP map with the combined BP map to generate an updated combined BP map for correcting X-ray image data sets during subsequent processes. Moreover, in some embodiments of the invention processor 36 uses the updated combined BP map to correct the image that the user used to identify the user-defined BP map.

The program run by processor 36 to identify the likely bad pixel set may take any of several different forms and, in the interest of simplifying this explanation, a very simple program will be described. Nevertheless, it should be recognized that the present invention contemplates far more complicated algorithms and processes for automatically identifying a likely bad pixel set.

One simple rule that may be used to identify a likely bad pixel is to compare the intensity signal value associated with a pixel to the intensity values associated with adjacent pixels. For example, when an X-ray beam is directed through a piece of substantially homogeneous flesh, it is expected that adjacent pixels receiving portions of the X-ray beam that pass through similar thicknesses of the homogeneous flesh will generate similar intensity signal values. For this reason, one exemplary rule may be that, assuming a maximum pixel intensity signal of 10 and a substantially homogeneous uniform thickness section of a patient's anatomy, adjacent pixel intensity values should be within three intensity units of each other in order to be valid. Here, the valid Intensity differential is referred to generally as an acceptable maximum pixel variance. For instance, where first and second adjacent pixels have seven and six unit intensity values, respectively, it would be assumed that both of the pixel values are valid and that corresponding detector pixels are operating properly.

Figure 3:
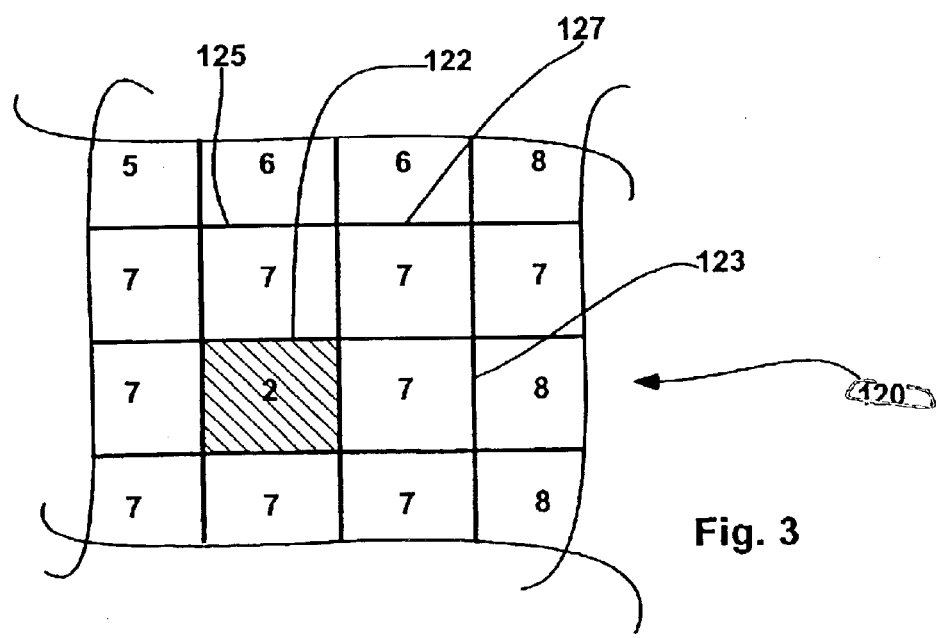
FIG. 3 is a schematic diagram of exemplary image pixels.

However, referring to FIG. 3, a sub-set of exemplary pixels is illustrated where numbers inside each pixel correspond to signal intensity values. As illustrated, one pixel 122 having an intensity value of 2 is surrounded by other pixels each having an intensity value of 7. In this case, when the intensity of pixel 122 is compared to the intensity of a pixel 123 to the right thereof as illustrated, applying the same maximum pixel variance rule as described above (e.g., that the maximum variance between adjacent pixels should be 3 units), it is assumed that one of the two pixels 122 or 123 is bad. By comparing other intensity signal values corresponding to pixels adjacent pixels 122 and 123 to the values of pixels 122 and 123, which of the two pixels 122 or 123 is bad should be ascertainable. For instance, as illustrated in FIG. 3, all pixels other than pixel 122 that surround pixel 123 have intensity signal values within the acceptable pixel variance (e.g., 3 units) of the value corresponding to pixel 123 while all signal values associated with pixels surrounding pixel 122 differ from the value associated with pixel 122 by more than 3 units. Here, application of the 3 unit variance rule easily identifies pixel 122 as likely bad.

Bad pixel identifying rules become more difficult to apply when there are groups of adjacent bad pixels. For example, referring again to FIG. 3, assume that each of pixel 122, pixel 123 and the two pixels thereabove 125 and 127 are bad and yield 2 unit intensity values. In this case a comparison of adjacent intensity values to identify likely bad pixels will not be as clear cut as in the case above. Nevertheless, by increasing the range of pixel values compared to identify bad pixels, accuracy will be increased. For instance, where comparison of immediately adjacent pixel values yield relatively uncertain results, the range of compared pixel values may automatically be extended to include the next most adjacent pixels surrounding a questionable pixel value. In some cases comparison of the next set may not yield more reliable results and in that case, the results may be discarded or the range of pixels compared may be increased further. However, where a larger pixel comparison yields more reliable results, the reliable results may be used to earmark specific pixels as likely bad for consideration by the system user.

The bad pixel identification tests will likely be different depending upon various factors. For example, the bad pixel identification test may vary as a function of the X-ray energy level used to generate an image data set. In this case, where a relatively low energy X-ray is used, the expected variance between adjacent pixel intensities will be relatively smaller than where relative high energy X-rays are used to generate signals.

As another example, the expected variance between adjacent pixel signal intensities will typically be a function of which portion of a patient's anatomy is being imaged. In this regard, where an object to be imaged (e.g., a patient's torso) is known to have structure that attenuates X-rays differently, the threshold level of acceptable variance between pixel intensities should be high. Similarly, where an object to be imaged is known to typically be void of structure/substance that attenuates X-rays differently within small regions, the threshold level of acceptable pixel variance for identifying a likely bad pixel should be relatively lower. Thus, it is contemplated that processor 36 will use different bad pixel identification threshold levels depending upon X-ray energy level and the type of imaging being performed in at least some embodiments of the invention. Other factors may affect the threshold level as well, and it should be understood that the two examples described above are not exhaustive and are only exemplary.

Referring now to FIG. 4, a bad pixel identification threshold table 100 is illustrated. Table 100 has three columns including an X-ray energy column 102, an imaging type column 104, and an acceptable maximum pixel variance column 106. Column 102 includes typical X-ray energy levels that are used to generate beam 17 in FIG. 1. For each energy level 1 in column 102, as its label implies, imaging type column 104 includes a list of imaging types that may be used with the energy level. For instance, with respect to energy level in column 102, column 104 includes cardiac, mammographic, angiographic, and so on. For each energy level/imaging type combination in columns 102 and 104, column 106 includes an acceptable maximum pixel variance value. For instance, as described above, one maximum variance may be three units and therefore, if adjacent pixels have pixel intensity signal values that differed by more than three units, it would be assumed that one of the adjacent pixels is bad.

Referring again to FIG. 1, prior to performing any of the inventive methods the combined BP map, pixel replacement program, BP identification program and BP identification threshold table 100 (see again FIG. 4) are stored in database 30 for access by processor 36. To perform an imaging process, a patient 19 is positioned on the support surface of table 20 and the patient and table are positioned between source 18 and detector 22 such that the portion of patient 19 to be imaged is located within the imaging area.

Figure 5:
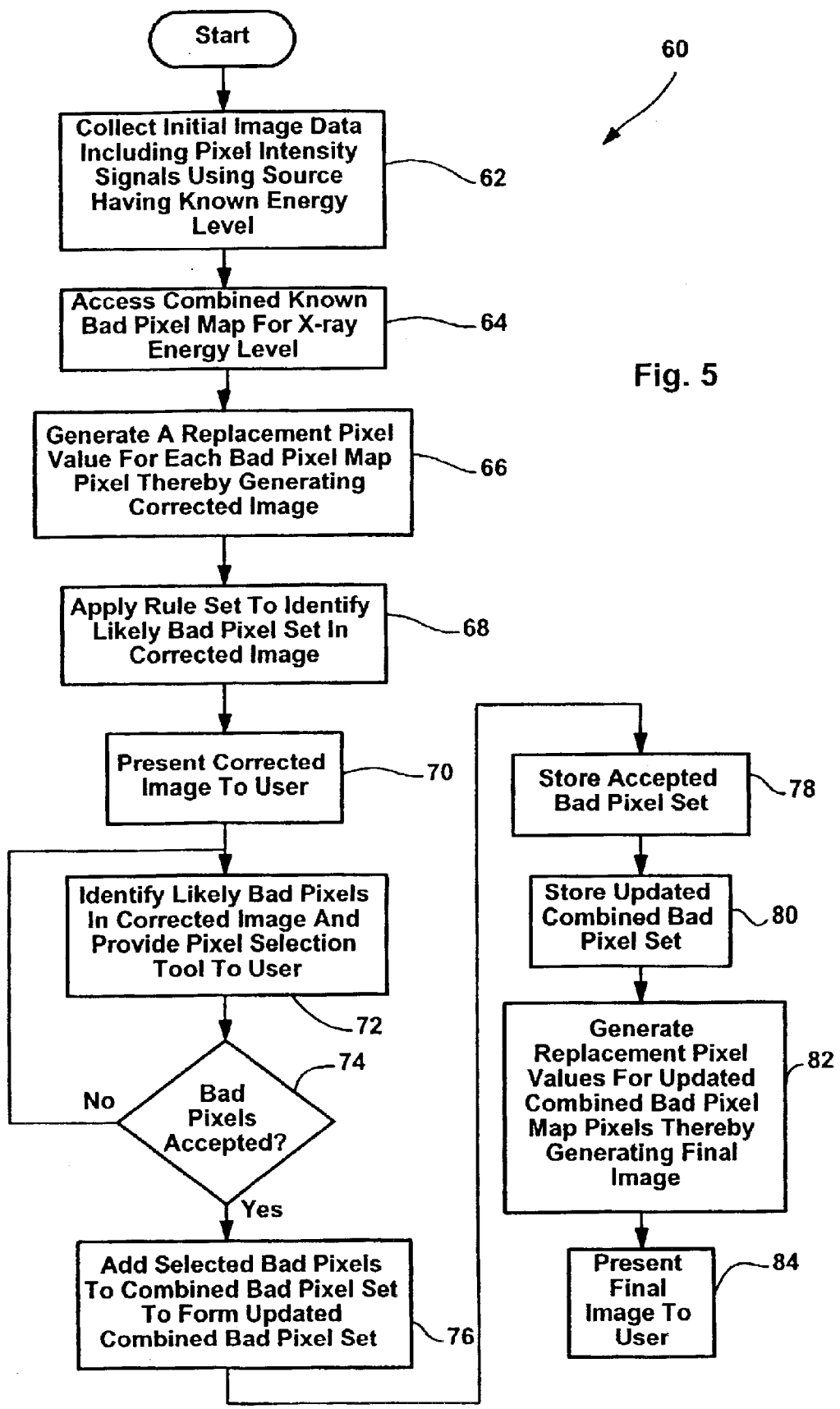
FIG. 5 is a flow chart illustrating one method according to the present invention.

Referring now to FIG. 5, an exemplary method 60 according to the present invention is illustrated. At block 62, source 18 is turned on to generate X-ray beam 17 having a known energy level that is directed through the portion of patient 19 to be imaged with X-rays passing through patient 17 impinging upon the detector surface of detector 22. Detector 22 generates an initial image data set corresponding to the detected X-rays. Circuitry 28 obtains the initial image data set and stores the set in database 30.

At block 64 processor 36 accesses the combined known bad pixel map for the X-ray energy level used during acquisition step 62 from database 30. At block 66 processor 36 runs the pixel value replacement program in database 30 to generate a replacement pixel value for each bad pixel in the combined bad pixel map. The replacement values are combined with the initial image data set pixel values corresponding to pixels that are not included in the combined bad pixel map to generate a corrected image data set which is also stored in database 30.

Referring still to FIG. 5 and also to FIG. 4, at block 68, processor 36 accesses the bad pixel identification threshold table 100 and identifies the acceptable maximum pixel variance of adjacent pixels in column 106 as a function of both the X-ray energy level used to generate the initial image data set and as a function of the imaging type performed (e.g., cardiac, mammography, etc.). Processor 36 uses the maximum pixel variance to identify the likely bad pixel set in the corrected image by running the BP identification program stored in database 30.

At block 70, processor 36 presents the corrected image to the user via display 12. At block 72, in at least some embodiments of the invention, processor 36 automatically highlights the likely bad pixels in the corrected image and provides pixel selection tools to the user including, for instance, the mouse control cursor 46 and acceptance and selection icons 50 and 52 (see again FIG. 2), respectively. In the alternative, the processor 36 may simply provide the corrected image to the user and offer the user an option to view the processor identified likely bad pixel set such as, for instance, by selecting the toggle-type icon 48 provided in space 42.

Continuing, at block 74, processor 36 determines whether or not any bad pixels have been accepted by the system user. As described above bad pixels may be selected by either accepting all of the processor identified bad pixels, selecting a subset of the likely bad pixels, selecting processor identified bad pixels and using selection tools to add additional user identified bad pixels to the processor identified pixels or by simply selecting bad pixels independent of the processor highlighted set. Where no bad pixels have been accepted, control passes back up to block 72 where the processor continues to display the image and the likely bad pixels. When bad pixels are accepted at block 74, control passes to block 76 where controller 36 adds the selected bad pixels to the combined bad pixel set to form the updated combined bad pixel set. At block 78, processor 36 stores the accepted bad pixel set as a user defined bad pixel set. At block 80, processor 36 stores the updated combined bad pixel set. At block 82 processor 36 again accesses the initial image data set in database 30 and for each pixel in the updated combined bad pixel map, generates a replacement pixel value. The replacement pixel values are combined with the original pixel values for pixels that are not in the updated combined bad pixel map to generate a final corrected image. At block 84 the final corrected image is provided to the user via the interface display 12.

Some embodiments of the invention include additional useful features that may be used to help a system user select an optimal user defined bad pixel map. One additional feature, a pixel variance threshold adjustment tool, allows a system user to manually modify the acceptable maximum pixel variance level applied by processor 36 when performing the BP identification program. In this regard, when a system user observes an image generated using the initial combined BP map along with highlighted processor identified likely bad pixels, the user may decide that a first sub-set of the highlighted pixels should be flagged as bad while a second sub-set interspersed with the first sub-set should not be marked as bad. Here, again assuming 300 processor identified likely bad pixels the process of manually selecting the first sub-set of pixels to be marked bad would be burdensome at best.

In the above example, in many cases most of the pixels in the second sub-set (e.g., the pixels that the user does not want to mark as bad) will have value variances with respect to adjacent pixel values that are smaller than the variances between pixel values in the first sub-set and adjacent pixel values. For instance, assuming processor 36 applied a maximum pixel variance of 3 units to identify the likely bad pixels, in most cases, the first pixel sub-set will include a greater percentage of pixels having variances of 4 units or greater than with the second sub-set.

Referring again to FIG. 2, a variance threshold interface tool 55 is provided in space 42 to allow a user to alter the variance applied by processor 36 when performing the BP identification process. Interface tool 55 includes up and down arrows for increasing and decreasing the applied variance, respectively. Where one of the variance arrows is selected processor 36 re-runs the BP identification program with the new variance and updates the likely bad pixel set highlighted in image area 40. The variance can be decreased as well as increased where a decrease in variance (e.g., from 3 units to 2 units) will cause the number of processor identified likely bad pixels to rise.

It is also contemplated that a user may use interface tool 55 along with other interface tools to select all pixels having relatively high value variances and to then provide more questionable likely bad pixels for closer scrutiny. For example, a user may increase the variance threshold to 5 units or greater which, in the above example, may reduce the original 300 likely bad pixel set to 75 likely bad pixels. Thereafter the user may wholesale select the 75 likely bad pixels (e.g., by selecting icon 50) and add those pixels to the user defined BP map. Next, the user may specify a variance of between 3 and 4 to display the remaining 225 pixels of the initial 300 likely bad pixels for more rigorous consideration. Here, the user may select a subset of the 225 pixels to be added to the user map prior to selecting icon 49 to store the user defined map.

To apprise the public of the scope of this invention, the following claims are made:

1. An apparatus for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, after signals are generated, the processor automatically using intensity signals corresponding to other than the bad pixel set to generate replacement intensity signals for each of the bad pixel set pixels thereby generating a corrected image, the apparatus for identifying additional bad pixels, the apparatus comprising:

a processor that, after the image data is collected, examines at least one of the initial image and the corrected image to identify a likely additional bad pixel set including pixels that have unexpected values; and an interface for indicating the likely bad set to a system user.

2. The apparatus of claim 1 wherein the interface also provides a tool for accepting at least a sub-set of the likely bad set wherein, when a sub-set is accepted by a user, the processor adds the accepted sub-set to the known bad pixel set to provide an updated bad pixel map.

3. The apparatus of claim 2 wherein, when a sub-set is accepted by a user, after the updated bad pixel map is provided, the processor uses he initial intensity signals corresponding to pixels other than the updated bad pixel map pixels to generate replacement intensity signals for each of the updated bad pixel map pixels to generate a final image and provides the final image to the user via the interface.

4. The apparatus of claim 2 wherein the updated bad pixel map is stored as the initial bad pixel map for subsequent signal correction.

5. The apparatus of claim 2 wherein the tool for accepting includes a tool that enables the user to accept the entire likely bad set.

6. The apparatus of claim 2 wherein the tool for accepting includes a tool that enables the user to add image pixels to and subtract image pixels from the likely bad set identified by the processor prior to accepting the sub-set.

7. The apparatus of claim 6 wherein the tool provides the corrected image to the user and indicates the likely bad set on the corrected image.

8. The apparatus of claim 1 wherein the processor identifies likely bad set pixels by, for each pixel, comparing pixel signal intensity to signal intensities of pixels proximate the specific pixel and, when a variance between the signal intensity corresponding to the specific pixel and signal intensities corresponding to the proximate pixels exceeds a threshold level, identifying the specific pixel as a likely bad set pixel.

9. The apparatus of claim 8 wherein the variance is user selectable.

10. The apparatus of claim 2 wherein the tool provides the corrected image to the user and indicates the likely bad set on the corrected image.

11. A method for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, after signals are generated, the processor automatically using intensity signals corresponding to other than the bad pixel set to generate replacement intensity signals for each of the bad pixel set pixels thereby generating a corrected image, the method for identifying additional bad pixels, the method comprising the steps of:

after the image data is collected, automatically examining at least one of the initial image and the corrected image via a processor to identify a likely bad pixel set including pixels that have unexpected intensity values; and indicating the likely bad set to a system user via an interface.

12. The method of claim 11 further including the steps of providing a tool for accepting at least a sub-set of the likely bad set via the interface and, when a sub-set is accepted by a user, adding the accepted sub-set to the known bad pixel map to provide an updated bad pixel map.

13. The method of claim 12 wherein, when a sub-set is accepted by a user, after the updated bad pixel map is provided, the method further includes the steps of using the initial intensity signals corresponding to pixels other than the updated bad pixel map pixels to generate replacement intensity signals for each of the defective pixels in the updated map to generate a final image and providing the final image to the user via the interface.

14. The method of claim 13 further including the step of storing the updated bad pixel map as the initial bad pixel map for subsequent signal correction.

15. The method of claim 13 wherein the step of providing a tool for accepting includes the step of providing a tool that enables the user to add image pixels to or subtract image pixels from the likely bad set identified by the processor prior to acceptance of the sub-set.

16. The method of claim 15 wherein the step of providing the tool further includes providing the corrected image to the user and indicating the likely bad set on the corrected image.

17. The method of claim 11 wherein the step of identifying includes identifying likely defective pixels by, for each pixel, comparing pixel signal intensity to signal intensities of pixels proximate the specific pixel and, when a variance between the signal intensity corresponding to the specific pixel and signal intensities corresponding to the proximate pixels exceeds a threshold level, identifying the specific pixel as a likely bad pixel.

18. The method of claim 12 wherein the step of providing the tool includes providing the corrected image to the user via the interface and indicating the likely bad set on the corrected image.

19. A method for use with a detector system including a solid state flat panel detector and an image processor, the detector including a plurality of pixels, each pixel generating an initial intensity signal, the initial signals together defining an initial image, the processor storing an initial bad pixel map that includes a known bad pixel set, the method comprising the steps of, after signals are generated:

examining initial intensity signals corresponding to other than the bad pixel set via the imaging processor to identify a likely bad pixel set including pixels that have unexpected values;

using the intensity signals corresponding to other than the bad pixel set to generate replacement intensity signals for each of the bad pixel set pixels thereby generating a corrected image;

providing the corrected image via an interface;

identifying the likely bad set on the corrected image; and monitoring the interface for selection of user identified bad pixels;

when user identified bad pixels have been identified, adding the user identified bad pixels to the bad pixel set to generate an updated bad pixel map;

using the intensity signals corresponding to other than the updated bad pixel map to generate replacement intensity signals for each of the updated bad pixel map pixels thereby generating a corrected image; and presenting the corrected image to the system user via the interface.

20. The method of claim 19 further including the step of storing the updated bad pixel map as an initial bad pixel map for subsequent use.

* * * * *